(12) United States Patent  
Nihoshi

(10) Patent No.: US 8,014,065 B2
(45) Date of Patent: Sep. 6, 2011

(54) MICROSCOPE APPARATUS WITH FLUORESCENCE CUBE FOR TOTAL-INTERNAL-REFLECTION FLUORESCENCE MICROSCOPY

(75) Inventor: Toshiaki Nihoshi, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/563,141

(22) Filed: Sep. 20, 2009

(65) Prior Publication Data

US 2010/0014158 A1 Jan. 21, 2010

Related U.S. Application Data

(63) Continuation of application No. PCT/JP2008/055627, filed on Mar. 18, 2008.

(30) Foreign Application Priority Data

Apr. 11, 2007 (JP) .................................. 2007-104054
Dec. 20, 2007 (JP) .................................. 2007-329046

(51) Int. Cl.
*G02B 21/06* (2006.01)
(52) U.S. Cl. ........................................ 359/388; 359/385
(58) Field of Classification Search .................. None
See application file for complete search history.

(56) References Cited

U.S. PATENT DOCUMENTS 7,187,494 B2 3/2007 Nishiwaki et al.
7,369,308 B2 * 5/2008 Tsuruta et al. ................ 359/388

FOREIGN PATENT DOCUMENTS

| JP | 2000098250 A | * | 4/2000 |
| JP | 2005-121796 A | | 5/2005 |
| JP | 2006-162994 A | | 6/2006 |
| JP | 2007-072391 A | | 3/2007 |

* cited by examiner

*Primary Examiner* — Arnel C Lavarias
(74) *Attorney, Agent, or Firm* — Miles & Stockbridge P.C.

(57) ABSTRACT

A microscope apparatus has an illumination optical system illuminating a sample with laser light from laser light sources. A fluorescence detection optical system detects fluorescence from the sample. Fluorescence cubes are interchangeably provided in an optical path of the illumination optical system and lead the laser light to the sample. An objective lens is also provided. At least one of the fluorescence cubes includes an optical member that makes a principal ray of the laser light substantially parallel to an optical axis of the illumination optical system and concentrates the laser light on a given position that is on a pupil position of the objective lens and separated from the optical axis, thereby providing a microscope apparatus capable of changing from a confocal microscope to a total-internal-reflection fluorescence microscope by exchanging a fluorescence cube used in the fluorescence microscope.

11 Claims, 6 Drawing Sheets

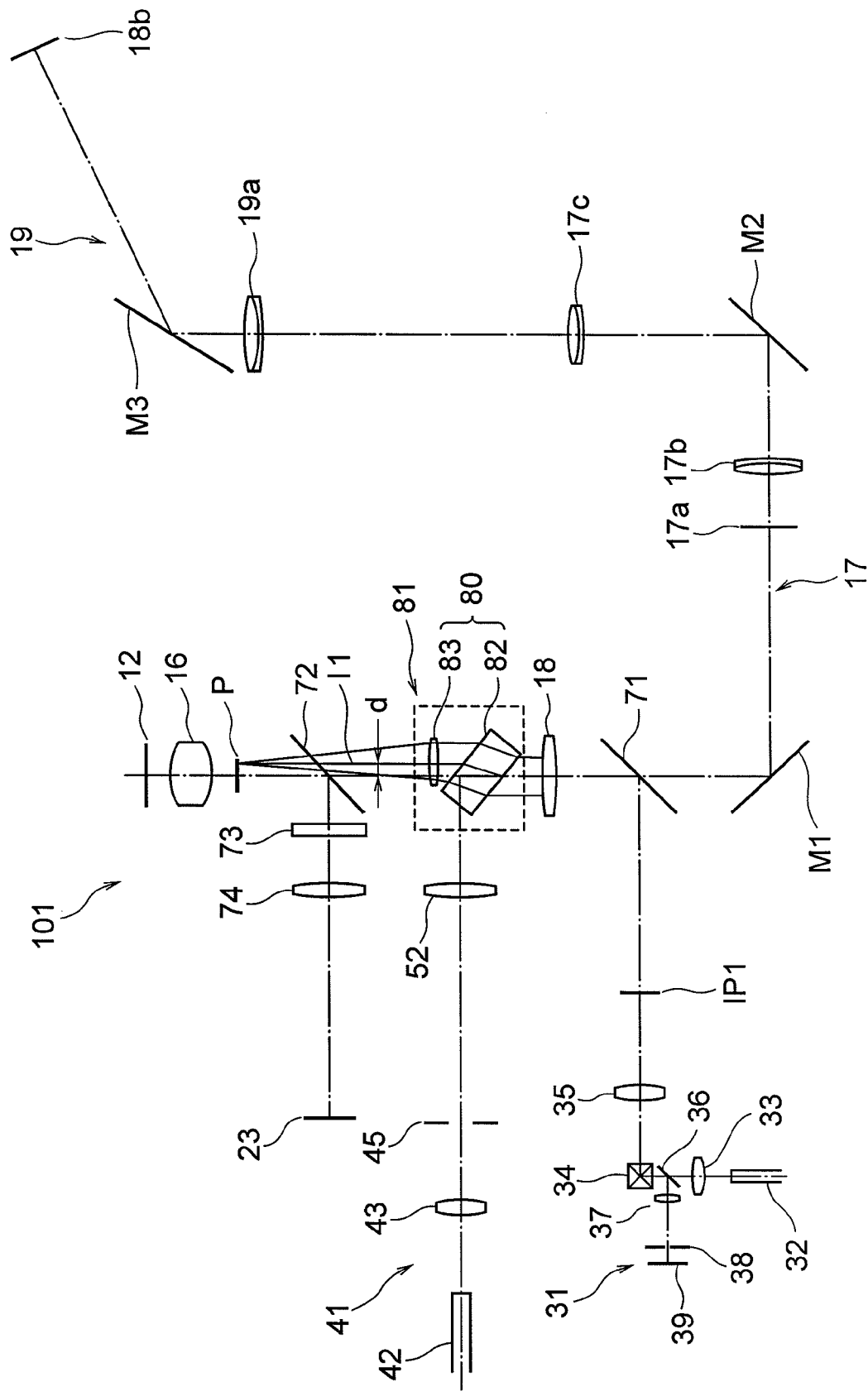

MICROSCOPE APPARATUS WITH FLUORESCENCE CUBE FOR TOTAL-INTERNAL-REFLECTION FLUORESCENCE MICROSCOPY

CROSS-REFERENCE TO RELATED APPLICATION

This application is a continuation of International Application No. PCT/JP2008/055627 filed Mar. 18, 2008.

TECHNICAL FIELD

The present invention relates to a microscope apparatus and a fluorescence cube installed therein.

BACKGROUND ART

A confocal microscope and a total-internal-reflection fluorescence microscope are widely used for observing living cells, and commonly use a laser light source. There has been proposed a microscope that can be commonly used for a confocal microscope and a total-internal-reflection fluorescence microscope (see, for example, Japanese Patent Application Laid-Open No. 2005-121796).

However, in the conventional microscope, upon changing a confocal microscope to a total-internal-reflection fluorescence microscope, an optical member for converging laser light to a total-internal-reflection condition area on a pupil position of an objective lens has to be inserted to an illumination optical system. Accordingly, a large exchanging mechanism is necessary, so that the microscope becomes large and expensive.

DISCLOSURE OF THE INVENTION

In order to solve the problem, according to a first aspect of the present invention, there is provided a microscope apparatus comprising: an illumination optical system that illuminates a sample with laser light from a laser light source; a fluorescence detection optical system that detects fluorescence from the sample; a plurality of fluorescence cubes that are provided on an optical path of the illumination optical system and leads the laser light to the sample; and an objective lens; at least one of the fluorescence cube including an optical member that makes a principal ray of the laser light substantially parallel to an optical axis of the illumination optical system and concentrates the laser light on a given position that is on a pupil position of the objective lens and separates from the optical axis.

According to a second aspect of the present invention, there is provided a fluorescence cube that is exchangeably disposed on an optical path of an illumination optical system of a fluorescence microscope, the fluorescence cube including an optical member that, upon being provided on an optical path of the fluorescence microscope, makes a principal ray of laser light illuminating a sample through an objective lens substantially parallel to an optical axis of the illumination optical system and concentrates the laser light on a given position that is on a pupil position of the objective lens and separates from the optical axis.

The present invention makes it possible to provide a microscope apparatus capable of exchanging from a confocal microscope to a total-internal-reflection fluorescence microscope by changing a fluorescence cube used in a fluorescence microscope, and a fluorescence cube capable of exchanging from a confocal microscope to a total-internal-reflection fluorescence microscope.

BRIEF DESCRIPTION OF THE DRAWINGS

FIGS. 4A, 4B, 4C are diagrams explaining an effect of an optical member of the microscope apparatus according to the first embodiment, in which
FIG. 4A is explaining a confocal scanning illumination state or an epi-illumination state,
FIG. 4B is explaining a total-internal-reflection illumination state,
and FIG. 4C is explaining a wedge prism effect.
FIG. 6 is a diagram showing an optical system of the microscope apparatus according to the second embodiment upon changing to a total-internal-reflection microscope.

EMBODIMENT FOR CARRYING OUT THE INVENTION

Microscope apparatus according to each embodiment of the present invention is explained below with reference to accompanying drawings.

First Embodiment

Figure 1:
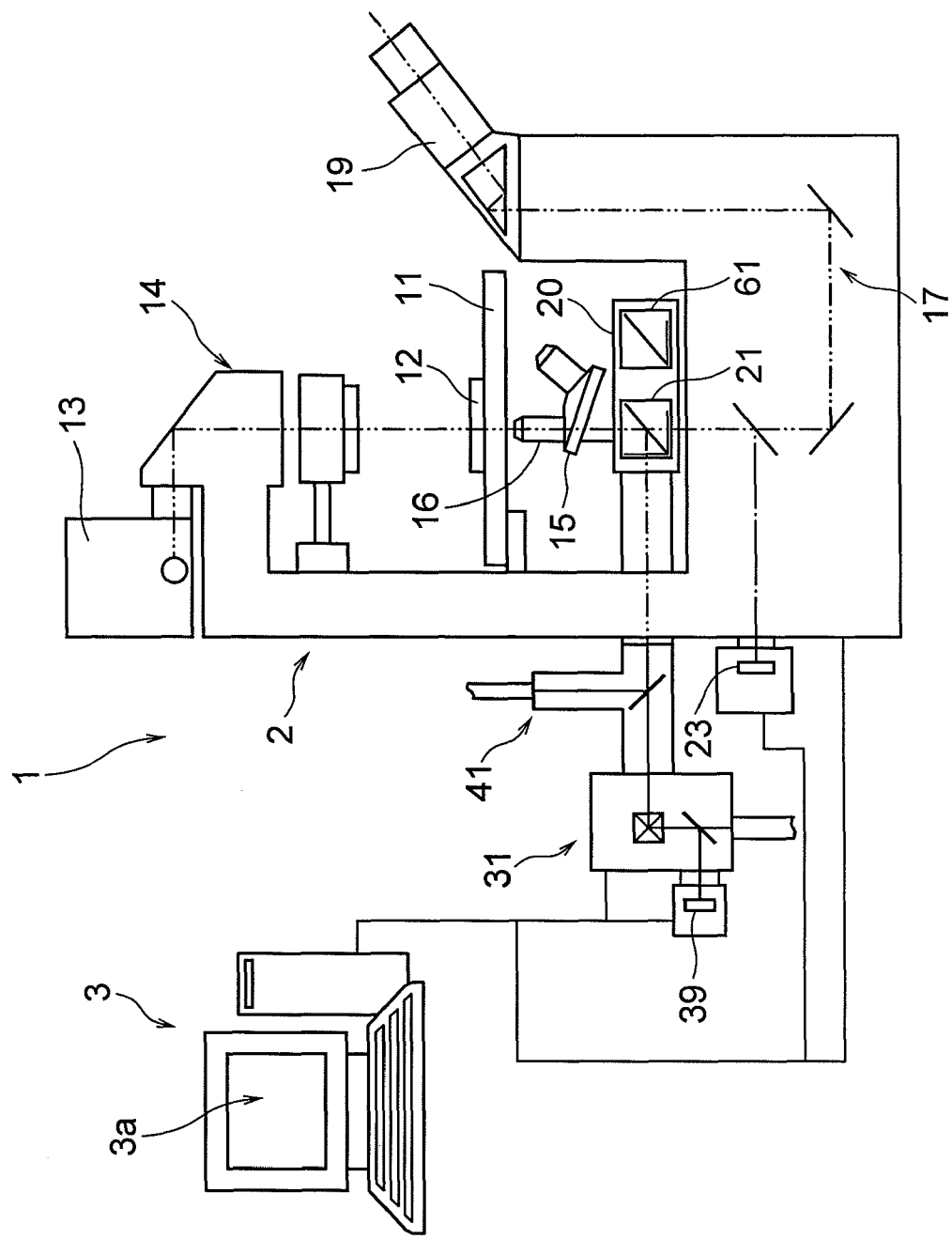
FIG. 1 is a schematic diagram showing a microscope apparatus according to a first embodiment.
Figure 2:
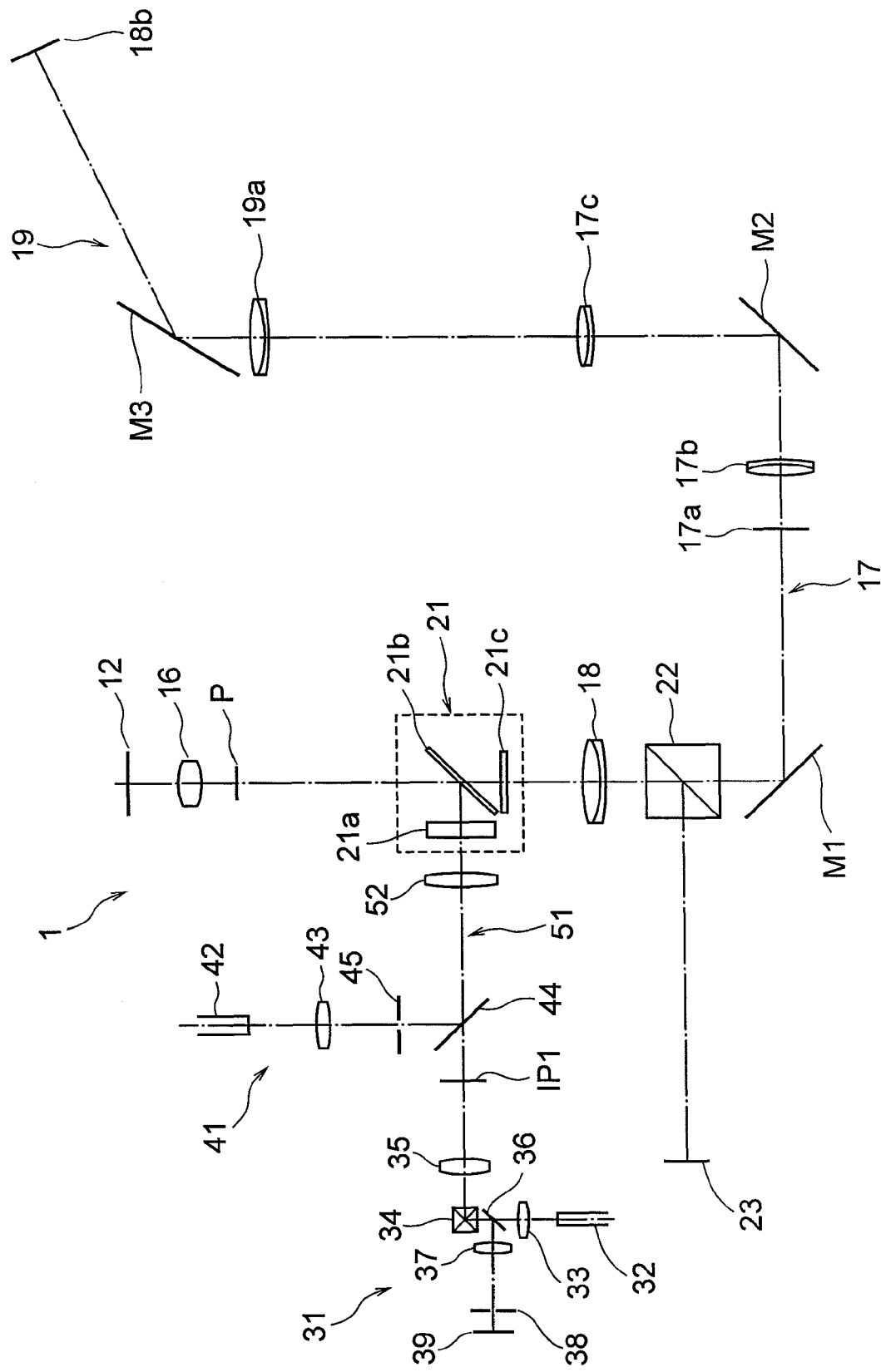
FIG. 2 is a diagram showing an optical system of the microscope apparatus according to the first embodiment.
Figure 3:
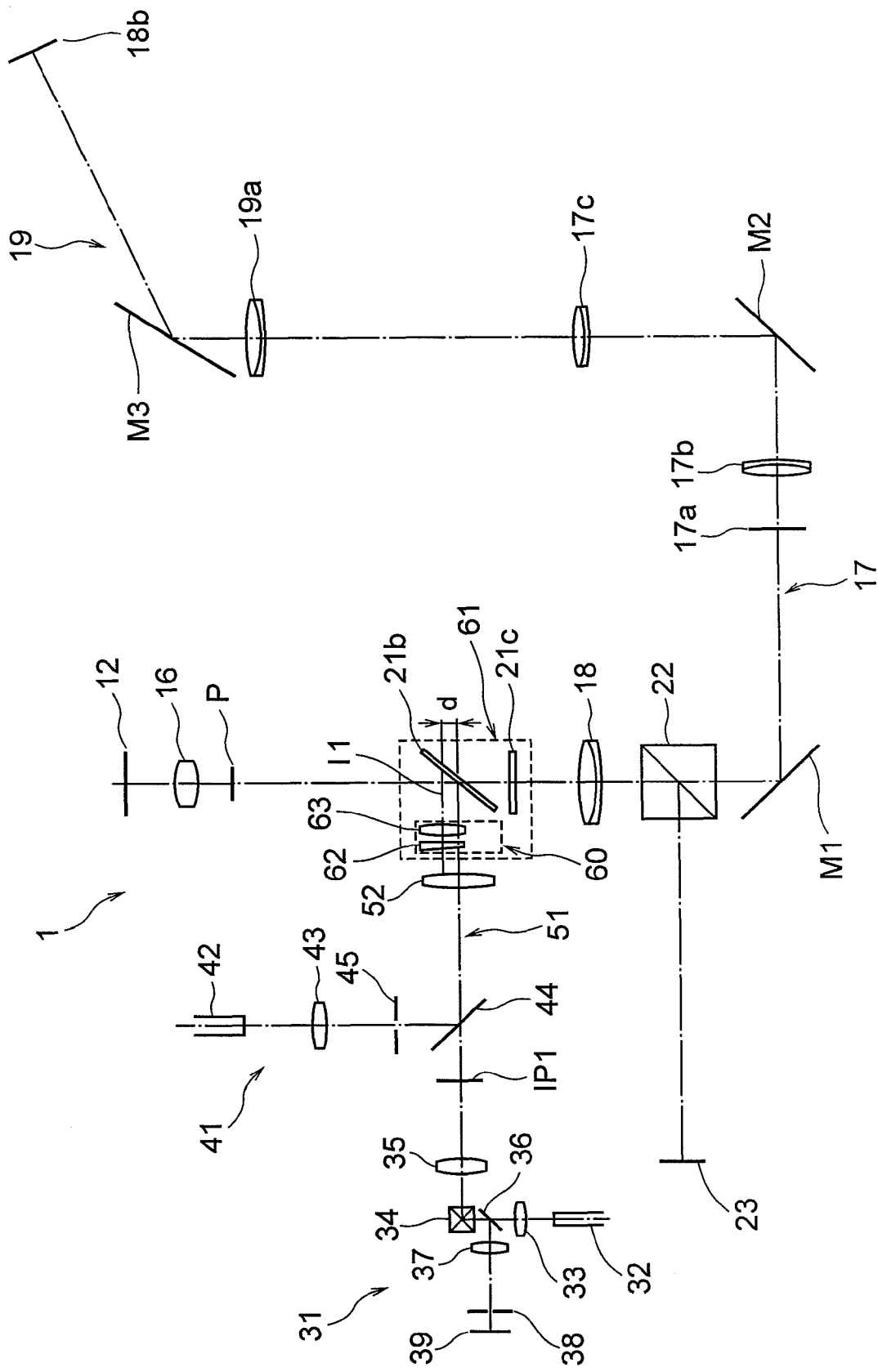
FIG. 3 is a diagram showing an optical system of the microscope apparatus according to the first embodiment upon changing to a total-internal-reflection microscope.
Figure 4A:
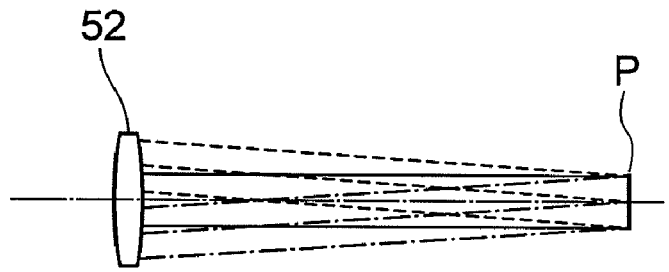
Figure 4B:
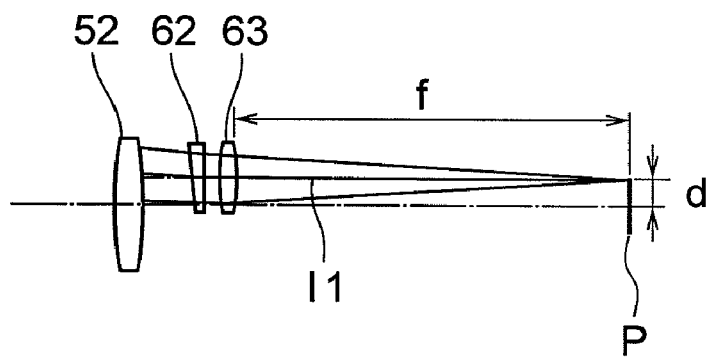
Figure 4C:
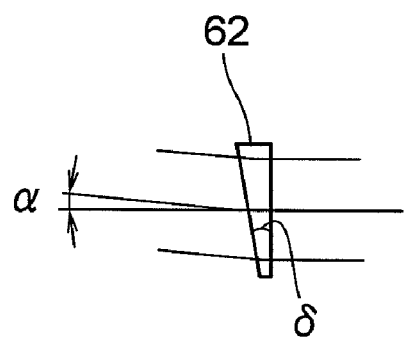

FIG. 1 is a schematic diagram showing a microscope apparatus according to a first embodiment. FIG. 2 is a diagram showing an optical system of the microscope apparatus according to the first embodiment. FIG. 3 is a diagram showing an optical system of the microscope apparatus according to the first embodiment upon changing to a total-internal-reflection microscope. FIGS. 4A, 4B, 4C are diagrams explaining an effect of an optical member of the microscope apparatus, in which FIG. 4A is explaining a confocal scanning illumination state or an epi-illumination state, FIG. 4B is explaining a total-internal-reflection illumination state, and FIG. 4C is explaining a wedge prism effect. In FIGS. 2 and 3, a transmission illumination optical system explained later is omitted.

In FIGS. 1 through 4C, a microscope apparatus 1 is composed of an inverted fluorescence microscope body 2 (hereinafter simply called a microscope), and a control apparatus 3 (hereinafter called a PC) constructed by a personal computer that controls various devices installed in the microscope 2.

The microscope 2 illuminates a sample 12 placed on a stage 11 by light from a transmission illumination light source 13 through a transmission optical system 14, and concentrates light passed through the sample 12 by an objective lens 16 installed in a revolver 15.

The light concentrated by the objective lens 16 forms an image on a first image plane 17a through an imaging lens 18 of an imaging optical system 17 and a mirror M1. The sample image formed on the first image plane 17a is formed on a second image plane 18b through a relay lens 17b, a mirror M2, a relay lens 17c, and a lens 19a in an eyepiece tube 19, and is observed by an observer through an unillustrated eyepiece. At this moment, a fluorescence cube 21 in a fluorescence cube holder 20 is removed from an optical path. A prism 22 is exchangeably disposed on the optical path, and is changed to a plane parallel plate having the same thickness upon observing the transmission image. In this manner, the microscope apparatus 1 can be used as a transmission microscope.

In the microscope 2 as shown in FIG. 2, a confocal scanning observation system 31 and an epi-illumination system 41 are disposed through a common illumination optical system 51.

A case where the microscope apparatus 1 is used as a scanning microscope (a scanning fluorescence microscope or a confocal scanning microscope) is explained below with reference to FIG. 2.

When the microscope apparatus 1 is used as a scanning microscope, a confocal scanning observation system 31 leads light from an unillustrated laser light source through an optical fiber 32, the laser light emanated from an end surface of the optical fiber 32 is made to be substantially parallel by a collector lens 33, and is incident on a two-dimensional scanner 34 that scans the laser light two-dimensionally on the sample 12. The laser light emanated from the two-dimensional scanner 34 forms an image on an image plane IP1 by a pupil relay lens 35. The laser light emanated from the image plane IP1 is made to be substantially parallel to the optical axis by an imaging lens 52 in the illumination optical system 51, and is incident on the fluorescence cube 21 exchangeably disposed on the optical path. When the confocal scanning observation system 31 is used, a dichroic mirror 44 that is removably disposed on the optical path of the illumination optical system 51 used in the epi-illumination system 41 explained later is removed from the optical path of the illumination optical system 51.

A wavelength selection filter 21a, a dichroic mirror 21b, and an emission filter 21c are installed in the fluorescence cube 21.

The laser light incident on the fluorescence cube 21 is selected a given excitation wavelength by the wavelength selection filter 21a and the dichroic mirror 21b, reflected in the direction of the objective lens 16, and incident on the objective lens 16 to be focused on the sample 12.

Fluorescence emanated from the sample 12 excited by the laser light is concentrated by the objective lens 16, incident on the fluorescence cube 21, and a given fluorescence is selectively transmitted by the emission filter 21c in the fluorescence cube 21. The transmitted given fluorescence is focused on an imaging device 23 through the imaging lens 18 and the prism 22 removably disposed in the imaging optical system 17, so that fluorescence image is captured by the imaging device 23. The image captured by the imaging device 23 is processed by the PC 3 shown in FIG. 1, and displayed on a monitor 3a. In this manner, the microscope apparatus 1 can be used as a scanning fluorescence microscope.

On the other hand, the laser light reflected from the sample 12 is concentrated by the objective lens 16, reflected by the dichroic mirror 21b in the fluorescence cube 21, goes backward of the illumination optical system 51, is incident on the two-dimensional scanner 34 to be descanned, is reflected by a beam splitter 36, and is incident on a photodetector 39 such as a PMT through an imaging lens 37 and a pinhole 38. On the basis of the intensity of each point detected by the photodetector 39, a two-dimensional image is formed by the PC 3 to be displayed on the monitor 3a. In this manner, the microscope apparatus 1 can be used as a confocal scanning microscope.

In the microscope apparatus 1, a fluorescence image captured by the imaging device 23 and a confocal image detected by the photodetector 39 can be superposed on the monitor 3a to be observed.

Then, a case where the microscope apparatus 1 is used as an epi-illumination fluorescence microscope is explained below with reference to FIG. 2.

In FIG. 2, light from an unillustrated light source in the epi-illumination system 41 is led by an optical fiber 42, the light emanated from an end surface of the optical fiber 42 is made to be substantially parallel light by a collector lens 43, and incident on the dichroic mirror 44 removably disposed in the illumination optical system 51 through a field stop 45. The light reflected from the dichroic mirror 44 is concentrated by the imaging lens 52 in the illumination optical system 51 to become substantially parallel light, and incident on the fluorescence cube 21 disposed exchangeably on the optical path. As the unillustrated light source, a laser light source, a high-pressure mercury vapor lamp, a xenon lamp, and the like may be used.

The laser light incident on the fluorescence cube 21 is selected a given excitation wavelength by the wavelength selection filter 21a and the dichroic mirror 21b, reflected in the direction of the objective lens 16, and incident on the objective lens 16 to be focused on the sample 12.

Fluorescence generated from the sample 12 excited by the laser light is concentrated by the objective lens 16, incident on the fluorescence cube 21, and a given fluorescence is selectively transmitted by the emission filter 21c in the fluorescence cube 21. The transmitted given fluorescence is focused on an imaging device 23 through the imaging lens 18 and the prism 22 removably disposed in the imaging optical system 17, so that fluorescence image is captured by the imaging device 23. The image captured by the imaging device 23 is processed by the PC 3 shown in FIG. 1, and displayed on a monitor 3a. In this manner, the microscope apparatus 1 can be used as an epi-illumination fluorescence microscope.

Then a case where the microscope apparatus 1 is used as a total-internal-reflection microscope is explained below with reference to FIG. 2.

The illumination system upon using the microscope apparatus 1 as a total-internal-reflection microscope uses the laser light in the above-described confocal scanning observation system 31. With inserting a fluorescence cube 61, which includes an optical member 60 for realizing total-internal-reflection illumination explained later, into the optical path, it can be used as a total-internal-reflection microscope.

As shown in FIG. 3, laser light from an unillustrated laser light source in the confocal scanning observation system 31 is led by the optical fiber 32, the laser light emanated from an end surface of the optical fiber 32 is made to be substantially parallel by a collector lens 33, and is incident on a two-dimensional scanner 34. In order to concentrate laser light to a total-internal-reflection condition area on the pupil position P of the objective lens 16, each tilt of XY mirrors in the two-dimensional scanner 34 is controlled by a control portion of the PC 3 shown in FIG. 1. The laser light, emanated from the two-dimensional scanner 34, whose optical axis has been shifted forms an image on an image plane IP1 by a pupil relay lens 35, and is incident on the fluorescence cube 61 disposed on the optical path through the imaging lens 52 in the illumination optical system 51.

The fluorescence cube 61 is composed of the optical member 60 constructed by a wedge prism 62 and a collector lens 63, the dichroic mirror 21b, and the emission filter 21c, and installed in the fluorescence cube holder 20 shown in FIG. 1 to be exchangeably disposed on the optical path. The wedge prism 62 and the collector lens 63 are disposed such that an optical axis I1 thereof is shifted from the optical axis of the illumination optical system 51 by a distance of "d" as shown in FIGS. 3 and 4B. The distance "d" corresponds to a position of NA that gives the total-internal-reflection condition of the objective lens 16.

The laser light incident on the fluorescence cube 61 becomes laser light whose principal ray that is coincide with the optical axis I1 is shifted by the distance "d" from the optical axis of the illumination optical system by means of the wedge prism 62, and is concentrated on a total-internal-reflection condition area having an annular shape on the pupil position P of the objective lens 16. The laser light concentrated on the total-internal-reflection condition area is incident on the sample 12 with an angle of incidence that generates total-internal-reflection on a boundary between the sample 12 and a glass substrate that holds the sample 12.

The laser light incident on the sample 12 with the total-internal-reflection angle generates evanescent wave on the boundary, and fluorescence excited from the evanescent wave is generated in the vicinity of the boundary of the sample 12. Since the wavelength of the laser light is selected by the laser light source, the wavelength selection filter 21a shown in FIG. 2 is not necessary.

Fluorescence generated on the sample 12 excited by the evanescent wave is concentrated by the objective lens 16, incident on the fluorescence cube 61, and a given fluorescence is selectively transmitted by the emission filter 21c in the fluorescence cube 61. The transmitted given fluorescence is formed an image on the imaging device 23 through the imaging lens 18 and the prism 22 removably disposed on the optical path of the imaging optical system 17, and the fluorescence image is captured by the imaging device 23. The image captured by the imaging device 23 is processed by the PC 3 shown in FIG. 1 to be displayed on the monitor 3a. In this manner, with exchanging the above-described fluorescence cube 21 to the fluorescence cube 61, and moving the optical axis I1 of the laser light substantially parallel by the distance "d" from the optical axis of the illumination optical system by means of the two-dimensional scanner 34 and the wedge prism 62, the microscope apparatus 1 can be used as a total-internal-reflection fluorescence microscope. Incidentally, upon performing total-internal-reflection illumination, the two-dimensional scanner 34 can be controlled such that the laser light scans the total-internal-reflection condition area having an annular shape on the pupil position P of the objective lens 16. With scanning the total-internal-reflection condition area having an annular shape by the laser light, excellent total-internal-reflection illumination can be carried out.

Then, transition to the total-internal-reflection illumination is explained with reference to FIGS. 4A, 4B, and 4C.

FIG. 4A shows a state of illumination light upon using as a scanning microscope or an epi-illumination fluorescence microscope. In this microscope, in each case where rays incident on the imaging lens 52 with (+) maximum angle of view shown by dotted lines, rays of center of the image shown by solid lines, and rays with (−) maximum angle of view shown by dashed lines, the rays are not concentrated on the pupil position P of the objective lens 16, and are substantially parallel.

On the other hand, in the illumination state of a total-internal-reflection microscope shown in FIG. 4B, the optical axis of the laser light is shifted from the optical axis of the illumination optical system 51 upward on the surface of FIG. 4B by the distance "d". The optical axis I1 of the laser light incident on the imaging lens 52 is tilted with respect to the optical axis of the illumination optical system 51 by the angle α as shown in FIG. 4C. The wedge prism 62 makes the tilt angle α substantially zero, and the optical axis I1 of the laser light and the optical axis of the illumination optical system 51 are made substantially parallel with a distance "d" apart with each other. After that the laser light is concentrated by the collector lens 63 on the total-internal-reflection condition area having an annular shape on the pupil position P of the objective lens 16. As a result, total-internal-reflection illumination can be realized.

As shown in FIG. 4C, the relation between the tilt angle α and a vertex angle δ of the wedge prism 62 is shown by the expression α=(n−1)×δ. Where n denotes refractive index of the medium composing the wedge prism 62.

In this manner, with arranging the fluorescence cube 61 composed of the collector lens 63 having a focal length f and the wedge prism 62 having a vertex angle δ corresponding to the inclination angle α of the optical axis I1 of the laser light according to a numerical aperture NA of the objective lens 16 into the fluorescence cube holder 21 shown in FIG. 1, and with exchangeably disposing the fluorescence cube 61 corresponding to the objective lens 16, it becomes possible to easily realize a total-internal-reflection illumination. In the shifting amount "d" of the optical axis I1 of the laser light, with controlling each tilt angle of XY mirrors in the two-dimensional scanner 34 in accordance with the objective lens 16 disposed on the optical path by means of the control portion of the PC 3 shown in FIG. 1, it becomes possible to set the position of the optical axis of the laser light corresponding to the change in the objective lens 16 and the fluorescence cube 61.

As described above, according to the microscope apparatus 1 of the first embodiment, with controlling the two-dimensional scanner 34 in the confocal scanning observation system 31 to a given inclination so as to shift the laser light from the optical axis of the illumination optical system 51, and with exchangeably inserting into the optical path the fluorescence cube 61 disposed in the fluorescence cube holder 20 that exchangeably holds a plurality of fluorescence cubes to be disposed on the optical path, it becomes possible to carry out total-internal-reflection observation. Moreover, it becomes possible to provide a microscope apparatus 1 capable of carrying out various observations such as a confocal scanning observation, a scanning fluorescence observation, an epi-illumination fluorescence observation, and a transmission observation.

Second Embodiment

Then a microscope apparatus according to a second embodiment is explained with reference to accompanying drawings. Schematic configuration of the microscope apparatus is similar to the first embodiment, so that figures and explanations are omitted.

Figure 5:
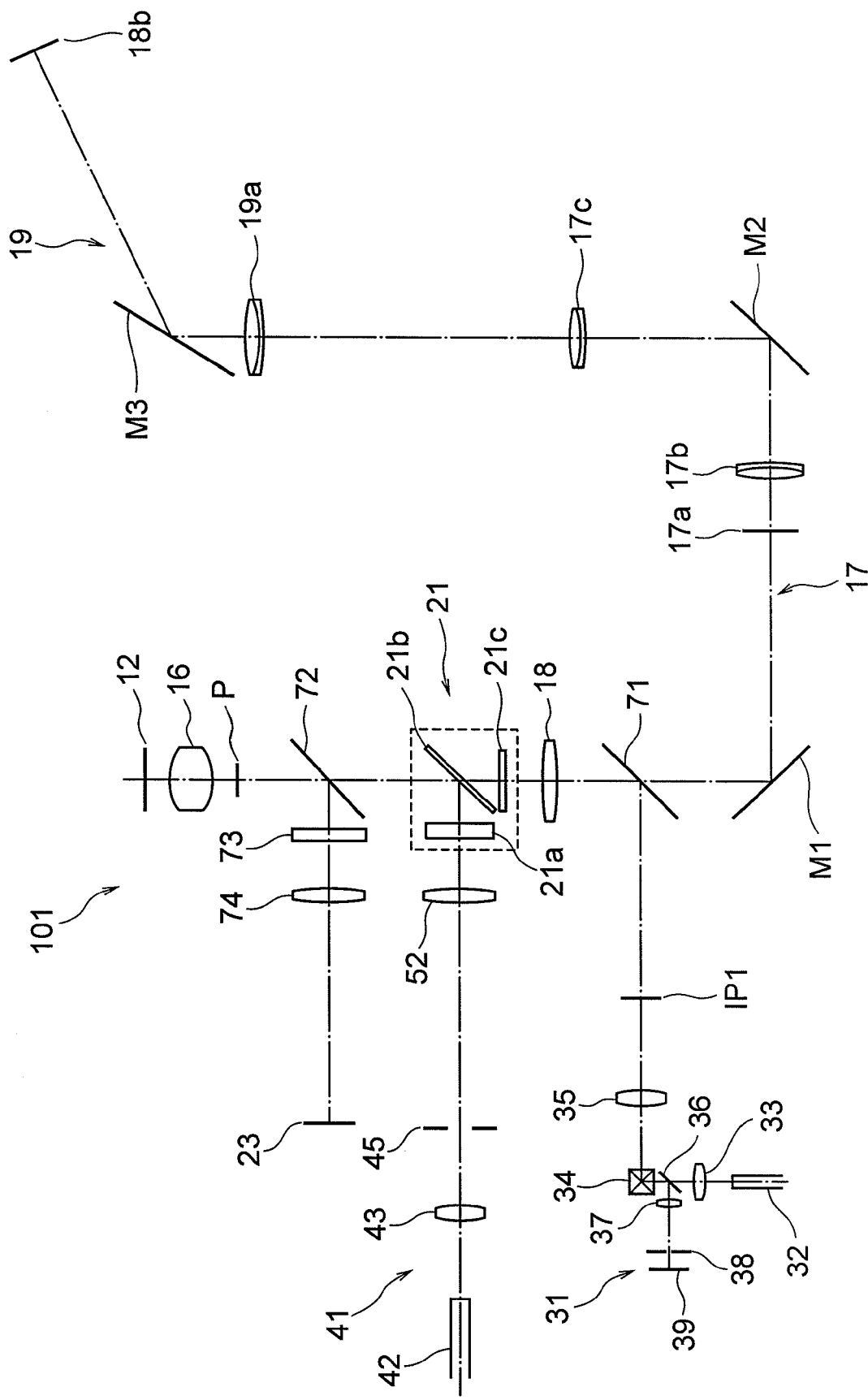
FIG. 5 is a diagram showing an optical system according to a second embodiment.

FIG. 5 is a diagram showing an optical system of the microscope according to the second embodiment. FIG. 6 is a diagram showing an optical system of the microscope apparatus according to the second embodiment upon changing to a total-internal-reflection microscope.

In FIG. 5, using procedures upon using the microscope apparatus 101 as a transmission microscope is the same as the first embodiment, so that duplicated explanations are omitted.

Then, a case where the microscope apparatus 101 is used as a scanning microscope is explained with reference to FIG. 5.

When the microscope apparatus 101 is used as a scanning microscope, in the confocal scanning observation system 31, laser light from an unillustrated laser light source is led by the optical fiber 32, the laser light emanated from an end surface of the optical fiber 32 is made to be substantially parallel light by the collector lens 33, and incident on the two-dimensional scanner 34 that scans two-dimensionally on the sample 12. The laser light emanated from the two-dimensional scanner 34 forms an image on the image plane IP1 by the pupil relay lens 35. The laser light emanated form the image plane IP1 is reflected by a dichroic mirror 71 removably disposed on the optical path, concentrated by the imaging lens 18 to become substantially parallel light, and incident on the objective lens 16 to be concentrated on the sample 12. In this instance, the fluorescence cube 21 exchangeably disposed on the optical path is removed from the optical path.

Fluorescence generated from the sample 12 excited by the laser light is concentrated by the objective lens 16, and a given fluorescence is selectively transmitted by a dichroic mirror 72 and an emission filter 73. The transmitted given fluorescence is formed an image on the imaging device 23 by an imaging lens 74, and the fluorescence image is captured by the imaging device 23. The image captured by the imaging device 23 is processed by the PC 3 shown in FIG. 1 to be displayed on the monitor 3a. In this manner, the microscope apparatus 101 is used as a scanning fluorescence microscope.

On the other hand, the laser light reflected by the sample 12 is concentrated by the objective lens 16, goes backward of the optical path, is incident on the two-dimensional scanner 34 through the imaging lens 18 and the dichroic mirror 71 to be descanned, is reflected by the beam splitter 36, and is incident on the photodetector 39 such as a PMT through the imaging lens 37 and the pinhole 38. A two-dimensional image is generated by the PC 3 based on intensity of each point detected by the photodetector 39, and displayed on the monitor 3a. In this manner, the microscope apparatus 101 can be used as a confocal scanning microscope. Incidentally, when the sample is observed with the above-described transmission illumination through the eyepiece tube 19, the dichroic mirrors 71, 72 and the fluorescence cube 21 or a fluorescence cube 81 explained later are removed from the optical path.

Moreover, in the microscope apparatus 101, the fluorescence image captured by the imaging device 23 and the confocal image detected by the photodetector can be superposed on the monitor 3a shown in FIG. 1 to be observed.

Then, a case where the microscope apparatus 101 is used as an epi-illumination fluorescence microscope is explained with reference to FIG. 5. In the second embodiment, the illumination optical systems of the confocal scanning observation system 31 and the epi-illumination system 41 are independently disposed except a portion.

In the epi-illumination system 41 shown in FIG. 5, light from an unillustrated light source is led by the optical fiber 42, and the light emanated from the end surface of the optical fiber 42 is made to be substantially parallel by the collector lens 43, concentrated by the imaging lens 52 through the field stop 45, and incident on the fluorescence cube 21 exchangeably disposed on the optical path.

The wavelength selection filter 21a, the dichroic mirror 21b, and the emission filter 21c are included in the fluorescence cube 21.

The laser light incident on the fluorescence cube 21 is selected by the wavelength selection filter 21a and the dichroic mirror 21b to become laser light having a given wavelength, reflected in the direction of the objective lens 16, and incident on the objective lens 16 to be focused on the sample 12.

Fluorescence generated by the sample 12 excited by the laser light is concentrated by the objective lens 16, and a given fluorescence is selected by the dichroic mirror 72 and the emission filter 73, formed an image on the imaging device 23 by the imaging lens 74, and a fluorescence image is captured by the imaging device 23. The image captured by the imaging device 23 is processed by the PC 3 shown in FIG. 1 to be displayed on the monitor 3a. In this manner, the microscope apparatus 101 can be used as an epi-illumination fluorescence microscope. As for the unillustrated light source, a laser light source, a high-pressure mercury vapor lamp, a xenon lamp, and the like may be used.

Then, a case where the microscope apparatus 101 is used as a total-internal-reflection microscope is explained with reference to FIG. 6.

An illumination while using the microscope apparatus 101 as a total-internal-reflection microscope uses the one in the above-described confocal scanning observation system 31, and in order to accomplish total-internal-reflection illumination, with exchangeably inserting the fluorescence cube 81 including an optical member 80 explained later into the optical path, it becomes possible to realize the apparatus being used as a total-internal-reflection microscope.

As shown in FIG. 6, the confocal scanning observation system 31 leads light from an unillustrated laser light source by the optical fiber 32, the laser light emanated from the end surface of the optical fiber 32 is made to be substantially parallel by the collector lens 33 to be incident on the two-dimensional scanner 34. Each inclination of the XY mirrors in the two-dimensional scanner 34 is controlled by the control portion of the PC 3 shown in FIG. 1 so that the optical axis of the laser light coincides with the optical axis of the confocal scanning observation system 31. The laser light emanated from the two-dimensional scanner 34 is formed an image on the image plane IP1 by the pupil relay lens 35. The laser light emanated from the image plane IP1 is reflected by the dichroic mirror 71 to become substantially parallel to the optical axis by the imaging lens 18, and incident on the fluorescence cube 81 exchangeably disposed on the optical path.

The fluorescence cube 81 is composed of an optical member 80 that is constructed by a plane parallel glass 82 disposed with a given inclination relative to the optical axis and a positive lens such as a collector lens 83, installed in the fluorescence cube holder 20, and exchangeably disposed on the optical path. The optical axis of the laser light emanated from the imaging lens 18 is shifted by the distance "d" to the shifted optical axis I1 by the plane parallel glass 82 inclined with respect to the optical axis. The distance "d" corresponds to the position of NA that gives total-internal-reflection condition on the pupil position P of the objective lens 16.

The laser light whose optical axis is shifted by the plane parallel glass 82 in the fluorescence cube 81 is concentrated on the total-internal-reflection condition area having an annular shape on the pupil position P of the objective lens 16. The laser light concentrated on the total-internal-reflection condition area is incident on the sample 12 with an angle of incidence that generates total-internal-reflection on a boundary between the sample 12 and a glass substrate that holds the sample 12.

The laser light incident on the sample 12 with the total-internal-reflection angle generates evanescent wave on the boundary, and fluorescence excited from the evanescent wave is generated in the vicinity of the boundary of the sample 12. Since the wavelength of the laser light is selected by the laser light source, the wavelength selection filter 21a shown in FIG. 5 is not necessary.

Fluorescence generated on the sample 12 excited by the evanescent wave is concentrated by the objective lens 16, and a given fluorescence is selectively transmitted by the dichroic mirror 72 and the emission filter 73. The transmitted given fluorescence forms an image on the imaging device 23 by the imaging lens 74, and a fluorescence image is captured by the imaging device 23. The image captured by the imaging device 23 is processed by the PC 3 shown in FIG. 1 to be displayed on the monitor 3a. In this manner, with exchanging the above-described fluorescence cube 21 to the fluorescence cube 81 and controlling the two-dimensional scanner 34 so that the optical axis of the laser light is coincide with the optical axis of the confocal scanning microscope 31, the microscope apparatus 101 can be used as a total-internal-reflection fluorescence microscope.

Moreover, with providing the fluorescence cube 81 including the optical member 80 constructed by the collector lens 83 having a focal length f and a plane parallel glass for shifting the optical axis in accordance with the numerical aperture (NA) of the objective lens 16 into the fluorescence cube holder 20 shown in FIG. 1, it becomes possible to easily realize total-internal-reflection illumination even if the objective lens 16 is changed.

As described above, according to the microscope apparatus according to the second embodiment, with controlling the two-dimensional scanner 34 in the confocal scanning observation system 31 such that the laser light coincides with the optical axis, and with exchanging the fluorescence cube 81, which includes the optical member 80 and is provided in the fluorescence cube holder 20 exchangeably providing plurality of fluorescence cubes, into the optical path, it becomes possible to carry out total-internal-reflection observation. Moreover, it becomes possible to provide a microscope apparatus 101 capable of carrying out various observations such as a confocal scanning observation, a scanning fluorescence observation, an epi-illumination fluorescence observation, and a transmission observation.

The present embodiment only shows a specific example for the purpose of better understanding of the present invention. Accordingly, it is needless to say that the invention in its broader aspect is not limited to the specific details and representative devices and can suitably be modified within the scope of the present invention.

What is claimed is:

1. A microscope apparatus comprising:
    an illumination optical system that illuminates a sample with laser light from a laser light source;
    a fluorescence detection optical system that detects fluorescence from the sample;
    a plurality of fluorescence cubes that are interchangeably provided in an optical path of the illumination optical system, at least one of the plurality of fluorescence cubes including a dichroic member therein which directs the laser light to the sample; and
    an objective lens;
    said at least one of the plurality of fluorescence cubes further including an optical member that makes a principal ray of the laser light substantially parallel to an optical axis of the illumination optical system and concentrates the laser light on a given position that is on a pupil position of the objective lens and separated from the optical axis,
    the optical member including a wedge prism and an imaging lens, in order, along a direction from an incident side of the at least one of the plurality of fluorescence cubes to the dichroic member therein,
    wherein the optical member is constructed such that, when said at least one of the plurality of fluorescence cubes is inserted into the optical path of the illumination optical system, laser light whose principal ray is tilted by a given angle with respect to the optical axis of the illumination optical system is incident on the wedge prism and exits from the wedge prism substantially parallel to the optical axis of the illumination optical system.

2. The microscope apparatus according to claim 1, wherein the laser light concentrated on the given position emanates from the objective lens and is incident on the sample with an angle of incidence that is a total-internal-reflection angle or more.

3. The microscope apparatus according to claim 2, wherein the illumination optical system further includes an epi-illumination optical system.

4. The microscope apparatus according to claim 1, wherein the illumination optical system further includes an epi-illumination optical system.

5. The microscope apparatus according to claim 1, wherein said optical member is arranged within said at least one of the plurality of fluorescence cubes between the laser light source and the dichroic member.

6. The microscope apparatus according to claim 1, wherein each fluorescence cube includes a respective dichroic member.

7. The microscope apparatus according to claim 1, wherein said optical member is arranged within said at least one of the plurality of fluorescence cubes with no further optical element in the optical path between the dichroic member and said optical member.

8. The microscope apparatus according to claim 1, wherein said at least one of the plurality of fluorescence cubes includes only one wedge prism.

9. A fluorescence cube that is exchangeably disposed in an optical path of an illumination optical system of a fluorescence microscope,
    the fluorescence cube including a dichroic member and an optical member that, upon being provided in the optical path of the fluorescence microscope, makes a principal ray of laser light for illuminating a sample through an objective lens substantially parallel to an optical axis of the illumination optical system and concentrates the laser light on a given position that is on a pupil position of the objective lens and separated from the optical axis,
    the optical member including a wedge prism and an imaging lens, in order, along a direction from an incident side of the fluorescence cube to the dichroic member therein,
    wherein the optical member is constructed such that, when the fluorescence cube is inserted into the optical path of the illumination optical system, laser light whose principal ray is tilted by a given angle with respect to the optical axis of the illumination optical system is incident on the wedge prism and exits from the wedge prism substantially parallel to the optical axis of the illumination optical system.

10. The fluorescence cube according to claim 9, wherein said optical member is arranged within the fluorescence cube with no further optical element in the optical path between the dichroic member and said optical member.

11. The fluorescence cube according to claim 9, wherein the fluorescence cube includes only one wedge prism.

* * * * *